(12) United States Patent
Kuntz et al.

(10) Patent No.: US 10,098,742 B2
(45) Date of Patent: Oct. 16, 2018

(54) COMPONENT CONSISTING OF CERAMICS, COMPRISING PORE CHANNELS

(71) Applicant: CeramTec GmbH, Plochingen (DE)

(72) Inventors: Meinhard Kuntz, Esslingen (DE);
Heinrich Wecker, Eckental (DE);
Alfons Kelnberger, Röthenbach (DE);
Kilian Friederich, Plochingen (DE);
Katia Biotteau, Lille (FR); Moritz Messmer, Stuttgart (DE)

(73) Assignee: CeramTec GmbH, Plochingen (DE)

( * ) Notice: Subject to any disclaimer, the term of this patent is extended or adjusted under 35 U.S.C. 154(b) by 0 days.

(21) Appl. No.: 14/892,855

(22) PCT Filed: May 23, 2014

(86) PCT No.: PCT/EP2014/060691
§ 371 (c)(1),
(2) Date: Nov. 20, 2015

(87) PCT Pub. No.: WO2014/187969
PCT Pub. Date: Nov. 27, 2014

(65) Prior Publication Data
US 2016/0106540 A1    Apr. 21, 2016

(30) Foreign Application Priority Data

May 23, 2013   (DE) .......................... 10 2013 209 584

(51) Int. Cl.
*A61F 2/28*        (2006.01)
*A61L 27/10*       (2006.01)
*A61L 27/50*       (2006.01)
*A61L 27/56*       (2006.01)

(52) U.S. Cl.
CPC .............. *A61F 2/2846* (2013.01); *A61F 2/28* (2013.01); *A61L 27/10* (2013.01); *A61L 27/50* (2013.01); *A61L 27/56* (2013.01); *A61F 2002/2839* (2013.01); *A61L 2430/38* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,629,464 A | * | 12/1986 | Takata | A61F 2/28 501/1 |
| 5,769,897 A | * | 6/1998 | Harle | A61F 2/0095 424/423 |
| 6,302,914 B1 | * | 10/2001 | Michelson | A61F 2/30744 606/247 |
| 6,605,293 B1 | * | 8/2003 | Giordano | A61F 2/2875 424/422 |
| 6,905,516 B1 | * | 6/2005 | Lemaitre | A61F 2/28 623/23.56 |
| 7,012,034 B2 | | 3/2006 | Heide et al. | |

(Continued)

FOREIGN PATENT DOCUMENTS

DE    199 40 717 A1    3/2001
DE    10 2008 001 402 A1    10/2009

*Primary Examiner* — Alvin Stewart
(74) *Attorney, Agent, or Firm* — James R. Crawford; Norton Rose Fulbright US LLP

(57) ABSTRACT

A ceramic component that consists of a shell, a filler material and pore channels that pass through the filler material, and can be used as an implant, particularly as a spacer.

20 Claims, 4 Drawing Sheets

(56) References Cited

U.S. PATENT DOCUMENTS

Figure 1:
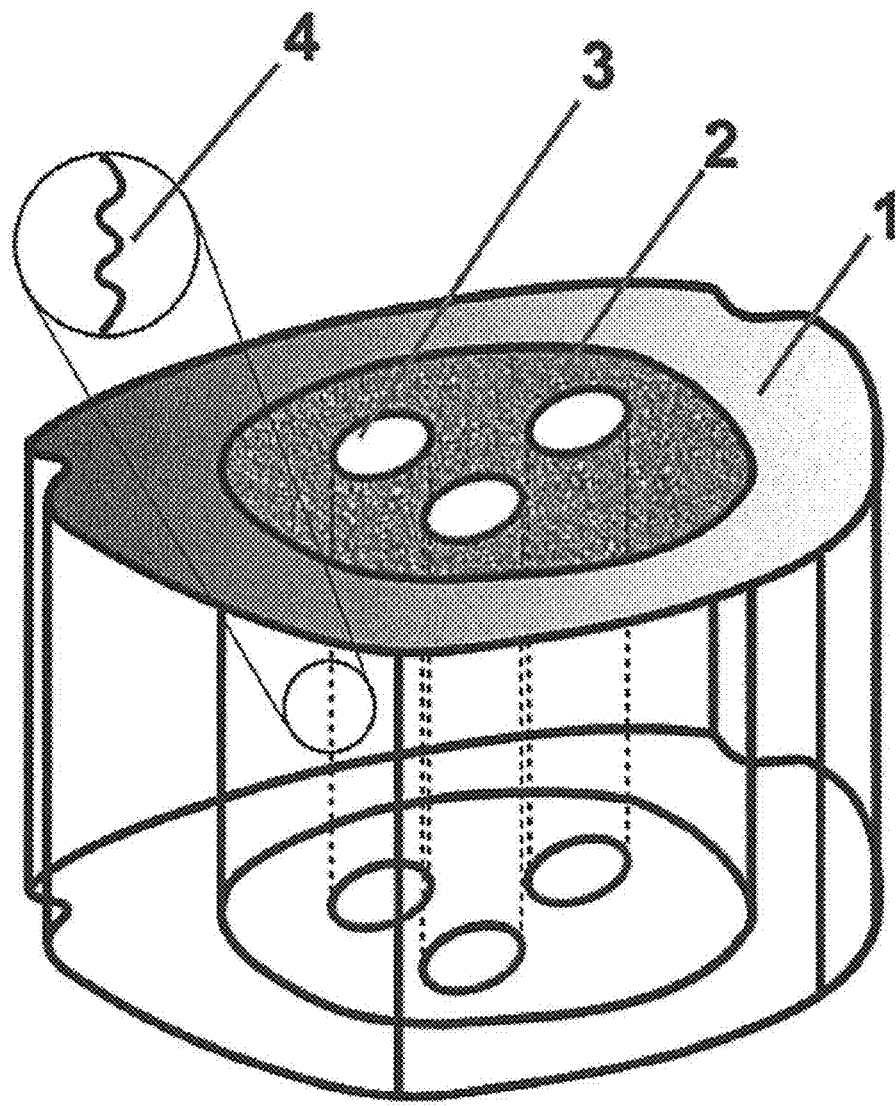

| | | | |
|---|---|---|---|
| 7,094,371 B2 | 8/2006 | Wei | |
| 8,414,654 B1* | 4/2013 | Ganey | A61F 2/28 623/16.11 |
| 8,702,808 B2* | 4/2014 | Teoh | A61F 2/28 623/23.61 |
| 8,916,228 B2* | 12/2014 | Oh | A61F 2/28 427/2.24 |
| 2002/0029084 A1* | 3/2002 | Paul | A61F 2/28 623/23.63 |
| 2002/0093124 A1* | 7/2002 | Wang | A61F 2/30 264/478 |
| 2002/0169066 A1 | 11/2002 | Cassidy et al. | |
| 2003/0065393 A1* | 4/2003 | Moumene | A61F 2/447 623/17.11 |
| 2003/0114936 A1* | 6/2003 | Sherwood | A61F 2/28 623/23.58 |
| 2003/0125739 A1* | 7/2003 | Bagga | A61F 2/4455 606/247 |
| 2003/0171822 A1 | 9/2003 | Wei | |
| 2004/0049270 A1* | 3/2004 | Gewirtz | A61F 2/28 623/17.11 |
| 2005/0015154 A1* | 1/2005 | Lindsey | A61B 17/68 623/23.46 |
| 2005/0042253 A1* | 2/2005 | Farrar | A61L 24/0036 424/426 |
| 2005/0112397 A1* | 5/2005 | Rolfe | A61B 17/8605 428/593 |
| 2005/0177238 A1* | 8/2005 | Khandkar | A61F 2/30767 623/17.11 |
| 2005/0228498 A1* | 10/2005 | Andres | A61F 2/4465 623/17.11 |
| 2006/0178748 A1* | 8/2006 | Dinger, III | A61B 17/1615 623/18.11 |
| 2007/0083268 A1* | 4/2007 | Teoh | A61F 2/2875 623/17.19 |
| 2007/0112434 A1* | 5/2007 | Hakamatsuka | A61F 2/28 623/23.5 |
| 2007/0203584 A1* | 8/2007 | Bandyopadhyay | A61F 2/28 623/23.5 |
| 2008/0057095 A1* | 3/2008 | Harlow | A61K 9/0024 424/422 |
| 2008/0213611 A1 | 9/2008 | Asgari | |
| 2009/0024223 A1* | 1/2009 | Chen | A61B 17/1604 623/23.63 |
| 2010/0009103 A1* | 1/2010 | Kuboki | A61F 2/28 428/34.6 |
| 2010/0137990 A1* | 6/2010 | Apatsidis | A61L 27/56 623/17.16 |
| 2010/0256758 A1* | 10/2010 | Gordon | A61F 2/28 623/16.11 |
| 2010/0268337 A1* | 10/2010 | Gordon | A61F 2/28 623/16.11 |
| 2010/0292146 A1* | 11/2010 | Seibl | A61F 2/28 514/8.8 |
| 2010/0310623 A1* | 12/2010 | Laurencin | A61F 2/28 424/423 |
| 2010/0331998 A1* | 12/2010 | Ringeisen | A61F 2/28 623/23.61 |
| 2011/0045279 A1 | 2/2011 | Heinl et al. | |
| 2011/0082551 A1* | 4/2011 | Kraus | A61F 2/30771 623/17.11 |
| 2011/0257753 A1* | 10/2011 | Gordon | A61F 2/28 623/18.11 |
| 2011/0313538 A1* | 12/2011 | Oh | A61L 27/56 623/23.61 |
| 2012/0150299 A1* | 6/2012 | Ergun | B29C 47/6037 623/17.11 |
| 2012/0185047 A1* | 7/2012 | Wooley | A61F 2/4465 623/17.16 |
| 2012/0330420 A1* | 12/2012 | Brodke | A61F 2/30767 623/17.16 |
| 2013/0030540 A1* | 1/2013 | Leibinger | A61F 2/28 623/20.32 |
| 2013/0178947 A1* | 7/2013 | Monaghan | A61L 27/56 623/23.55 |
| 2014/0114419 A1* | 4/2014 | Dunworth | A61F 2/442 623/17.16 |
| 2014/0121776 A1* | 5/2014 | Hunt | A61F 2/4455 623/17.16 |
| 2014/0195001 A1* | 7/2014 | Grohowski, Jr. | B22F 3/1137 623/23.5 |
| 2014/0288650 A1* | 9/2014 | Hunt | A61F 2/30907 623/16.11 |
| 2015/0010501 A1* | 1/2015 | Crawford | A61K 35/12 424/85.2 |
| 2015/0238321 A1* | 8/2015 | Pflum | A61F 2/441 623/17.12 |
| 2015/0289979 A1* | 10/2015 | Gabele | A61L 27/446 623/23.55 |
| 2015/0297349 A1* | 10/2015 | Butscher | A61F 2/28 623/23.61 |
| 2016/0067381 A1* | 3/2016 | Wecker | A61L 27/10 623/17.16 |
| 2016/0114079 A1* | 4/2016 | Samaniego | A61L 27/54 424/549 |
| 2016/0135955 A1* | 5/2016 | Henderson | A61L 27/16 623/23.61 |
| 2016/0151539 A1* | 6/2016 | Anderson | A61L 27/3608 623/23.5 |
| 2016/0262894 A1* | 9/2016 | Cronstein | A61F 2/28 |
| 2016/0324642 A1* | 11/2016 | Maria de Peppo | A61K 35/12 |
| 2017/0007406 A1* | 1/2017 | Cui | A61F 2/28 |

* cited by examiner

COMPONENT CONSISTING OF CERAMICS, COMPRISING PORE CHANNELS

This application is a § 371 of International Application No. PCT/EP2014/060691filed May 23, 2014, and claims priority from German Patent Application No. 10 2013 209 584.8 filed May 23, 2013.

The subject matter of the present invention is a ceramic component that consists of a shell, a filler material and pore channels that pass through the filler material. This component can preferably be used as an implant and in particular as a spacer.

Porous materials are particularly suitable for the attachment and growth of new cell tissue such as bone cells. The porous component should consist of a biocompatible material that is capable of bearing loads, promotes biological cell attachment, the propagation of cells and the biological function thereof. This requires that a sufficient supply with biological liquids and nutrients is ensured at the site of the formation of new cells. For these reasons, the porous components should have a proportion of percolating pore volume.

Moreover, the pore size should fall within the range of the sizes of the newly formed cells. In addition, the component must be sufficiently stable to withstand the operation and the initial load in vivo without any damage.

In the past, various techniques for generating porous components and in particular ceramic components with a defined porosity were used. So far, however, no method exists that could be used to produce large numbers of these components with a reliable design at low costs and within a short time.

It is the object of the present invention to provide a component that promotes the form-locking growing on and/or in of cells in a particular way and to provide a method, by means of which large numbers of this component can be produced at low costs within a short time. At the same time, the component should ensure a primary and secondary strength that is considerably improved compared to the prior art.

The solution according to the invention provides a component/an implant that is designed as follows and preferably consists of ceramics:

The shell consists of a load-bearing, high-strength, dense, biocompatible material. The shell is designed such that it can fully accommodate the external forces acting on the component even without a filling material. The pore volume content of the shell is preferably less than 3 vol %, preferably less than 2 vol % and particularly preferably less than 1 vol %.

The implant contains a filling of a porous material of the same or a similar kind, wherein the porosity is present in a random form, occupies a volume content of 15-90 vol %, preferably of 20-70 vol % and particularly preferably of 25-50 vol %, and forms a percolating network, i.e. an interconnected network that is permeable to liquids. The pore size in the porous filling material is in a range of 2 to 400 µm, preferably in an order of magnitude of 5 to 200 µm.

Although the porous filling material should have a permeable, percolating pore network, however, at the same time the pore structure and the pore volume content are preferably realised in such a way that a material with a comparatively high residual strength is obtained. The compressive strength of the porous filling material is preferably >250 MPa, particularly preferably >500 MPa. As a result, unlike sponge- or foam-like materials, a comparatively solid and break-proof substrate is available to the growing bone. By this means, according to the invention, a high primary and secondary strength, i.e. strength during the ingrowth process and after the ingrowth process, of the implant is achieved. On the basis of this concept, in this invention the pore volume content of the filling material is particularly preferably limited to a maximum of 50%.

Moreover, defined directed pore channels, which are orientated in the preferential direction over the entire height of the component, pass through the porous filling material of the component. The channels may extend in a straight line or may be meandering. The diameter of the pore channels is between 0.1 and 2 mm, depending on the size of the cells that are supposed to grow in. Preferably, the diameter of the pore channels is between 0.3 and 1 mm.

The pore channels are designed to be in liquid exchange communication with the porous filling material. This may be achieved for example on account of the fact that the pore channels cut through the porosity structure of the filling material are in hydraulic communication with these through openings thus generated in the wall of the pore channels.

The wall of the pore channels is designed in such a way that on the one hand liquid can enter through the porous ceramic filling material and further a very pronounced surface roughness with a medium roughness depth of Rz 10-250 µm, preferably Rz 20-200 µm (determined according to DIN EN ISO 4287) is present. Thus, an intense interlocking with the structure of the walls of the pore channels is made possible.

Biocompatible materials that can be used for the component or the implant comprise in principle all the materials known from implantation technology, such as metals, in particular Ti and the alloys thereof, polymers such as poly ethyl ethyl ketone (PEEK) or polyethylene (PE) and of course ceramic materials such as oxide and nitride ceramics.

Particularly preferably, the implant is made from a ceramic.

By means of the solution according to the invention, the bone preferably grows into the pore channels, in an ideal case from both sides of the channels with an ultimate connection in the centre. However, for the anchoring of the components in the bone it is sufficient for the bone to grow only a certain distance into the channel, for example to a depth of approx. 1 mm.

In contrast, in the porous filling material there tends to be no or only very little ingrowth. The pore size is too low so as to allow the formation of new bone cells. However, due to the preferably hydrophilic nature of the ceramic material, the percolating porosity is rapidly completely filled with the body's own media, for example synovial fluid. This contributes to an optimal supply of the formation of new bone cells in the directed pore channels, since the pore channels are in hydraulic communication with the porosity of the filling material.

By means of the use according to the invention of a porous ceramic with a percolating porosity, nutritional medium can be transported via capillary forces. The growing bone cells are thus supplied with nutrients in an ideal manner. The porosity of the filling material and thus in particular of the internal walls of the continuous pore channels can, according to the invention, be designed such that a rough surface with ideal conditions for bone growth can be achieved.

The hydraulic communication between the pore channels and the porosity of the filling material thus advantageously allows the supply of the ingrowing bone cells at the site of their formation. This means that also bone cells that have already grown far into the implant can still be optimally supplied. This is oftentimes not the case with the porous materials known from the prior art, because no independent liquid communication paths are available.

Thus, according to the invention, up to four functions can be fulfilled at the same time:

1. The shell ensures strength.
2. The channels offer an optimal size for bone ingrowth.
3. The percolating porous ceramic is permeable to the body's own media and thus supports the nutrient supply of the bone cells growing in the pore channels.
4. The favourable surface topography of the channel walls allows a form-locking anchoring of the component during the ingrowth of the bone cells.

The component/implant according to the invention can therefore preferably be produced by means of a ceramic two-component injection moulding process. In the course of this, two plastifiable mixtures of ceramic powder and wax-like polymer preparations, so-called feedstocks, are produced. A first feedstock comprises the mixture of ceramic powder and polymer preparation, whereas the second feedstock additionally comprises pore generators.

The first feedstock is prepared such that after forming, debinding and sintering, a solid, dense ceramic body is obtained. This will form the load-bearing shell in the later component.

The second feedstock also comprises ceramic powder and a wax-like polymer preparation. However, in addition also combustible organic and inorganic pore generators are admixed ("fugitive spacers"). Upon formation, debinding and sintering, a porous ceramic body with a percolating pore network is obtained, which forms the porous filling in the component. The ceramic powder for the second feedstock is selected such that a tough bond is formed with the dense ceramic of the first feedstock. In this connection, a ceramic of the same kind may be advantageous but is not absolutely necessary. This means that for the first and the second feedstock, the same mixture of ceramic powder or a mixture of another ceramic powder may be used, with the use of the same mixture being preferred.

Preferably, oxide ceramics may be used for the component, particularly preferably ZTA (zirconia toughened alumina) ATZ (alumina toughened zirconia), compound materials on the basis of zirconium oxide with other reinforcement components, or TZP (tetragonal zirconia polycrystal). These ceramics are advantageous, inter alia, because they are hydrophilic and because they offer optimal conditions for body fluids to enter into the pore space. However, also biocompatible non-oxide ceramics such as e.g. silicon nitride fall into the scope of the invention.

Within the context of the present invention, "ceramic of the same type" is understood to be a ceramic that consists of the same ceramic basic components. It is also particularly preferred if the proportions of the ceramic basic components are substantially the same, i.e. within the limits of +/−10 vol % per proportion.

The two elements of the component are also injected, from various feedstocks, in one process into a mould, as a result of which the elements are in close physical contact with each other. This composite is subsequently debound and sintered. What is obtained is a monolithic body that has a solid, load-bearing shell and a porous filling material that is rigidly connected therein.

As pore generators, in principle any substances may be used that have a sufficient form and temperature resistance for the two-component injection moulding process of ceramic materials. Of course, pore generators have to be combustible, preferably without leaving residues, at the sintering temperatures of the ceramic.

The dimensional stability of the pore generators during the manufacturing process is essential. The pores should be permeable to fluid and should be percolating, so that any pore generators that are highly deformed by the injection moulding process are not to be tolerated. Further, the pore generators, or the pores generated thereby, must not shrink in an uncontrolled manner during the entire process, including the sintering.

Preferred pore generators within the context of the present invention, and without loss of generality, are as follows: maize semolina, melamine resin particles, polyamide particles, carbon particles, glassy carbon particles, carbon fibres, poppy seeds, cereal flour, in particular wheat flour and/or potato starch. Of course, also combinations of different pore generators may be used in a feedstock, e.g. spherical particles in combination with fibrous particles.

The pore channels may be produced by way of a particular technological design of the injection moulding tool and/or by post-processing the green body or the finished sintered body.

For the design of the injection moulding tool, the latter is provided with pin-like components which leave channel-like structures after the demoulding in the green body. The pins may additionally be provided with a surface structure, which during the deforming is correspondingly formed on the surface of the green body and thus leaves the desired rough structure.

The pore channels can also be generated by means of the directed introduction of combustible small rods which are combusted during sintering like the above-described pore generators. The small rods may for example be made from a polymer material.

A component/implant thus produced may for example be used as a spacer, i.e. as a spinal implant, for example after a spinal discectomy.

The invention will be explained in more detail below by means of examples. FIG. 1 shows a schematic embodiment of an implant according to the invention. The implant includes a solid, load-bearing shell 1 that laterally surrounds a porous filling material 2. The porous filling material 2 is exposed on the top and the bottom sides of the implant. The load-bearing shell has a pore volume proportion of less than 1 vol %.

The porous filling material 2 has a pore volume proportion that is between 15 and 90 vol %. The indicated volume proportion only relates here to the porous material itself, without considering the pore channels. The porosity of the filling material is percolated, i.e. the pores are always at least partially, preferably predominantly in communication with each other and allow body fluids to enter and to be transferred and/or to be circulated. In other words, this porosity forms a coherent network that can be filled with fluid. The pores preferably have a diameter in a range between 5 and 200 µm.

Moreover, continuous pore channels 3 pass through the porous filling material and are in this embodiment in contact with the environment through the top and bottom sides of the implant. In the implanted condition, the pore channels allow bone material to grow into and onto the implant. The pore channels 3 are in hydraulic communication with the above-described percolating pore network. The pore network is filled with body fluids on account of capillary forces. Due to the connection of pore channels and percolating porosity, these body fluids will also get into the inside of the pore channels, even if these have already been partially filled with newly formed bone material. Thus, the supply of the ingrowing bone cells with nutrients is ensured at any stage of the ingrowth.

Reference numeral 4 refers to an enlarged schematic section out of a wall of a pore channel. The wall of the pore channel is structured or roughened, so that the newly formed bone material can interlock with the implant. This interlocking affords an improved retention between the implant and the bone material.

Figure 2A:
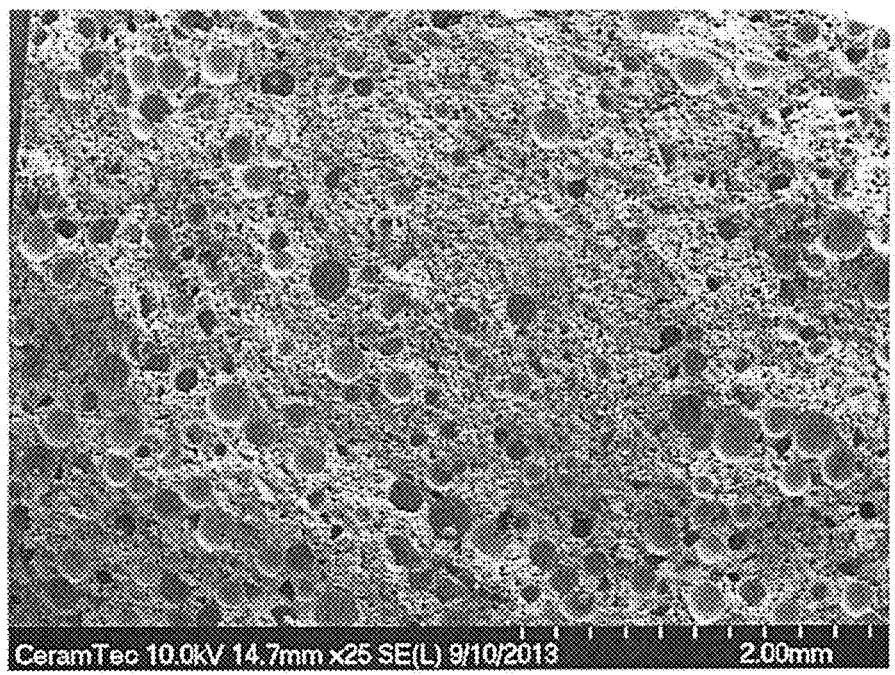

FIG. 2A shows a scanning electron micrograph of a broken-up section of a porous filling material according to the invention. An yttrium-stabilised TZP ceramic was used as the material. The individual pore sizes are very different and are in a range between 20 and 300 µm. The porosity was achieved by combusting spherical carbon particles.

Figure 2B:
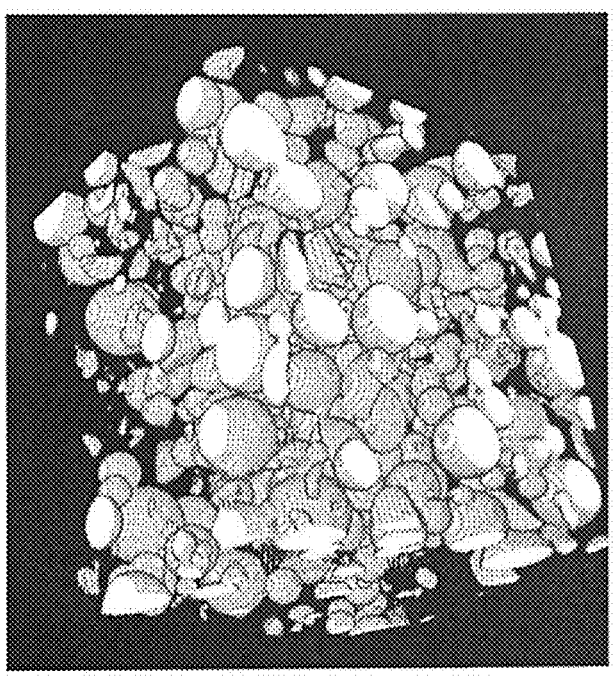

FIG. 2B shows a computer tomographic reconstruction of the percolating network of the filling material shown in FIG. 2A.

Figure 3A:
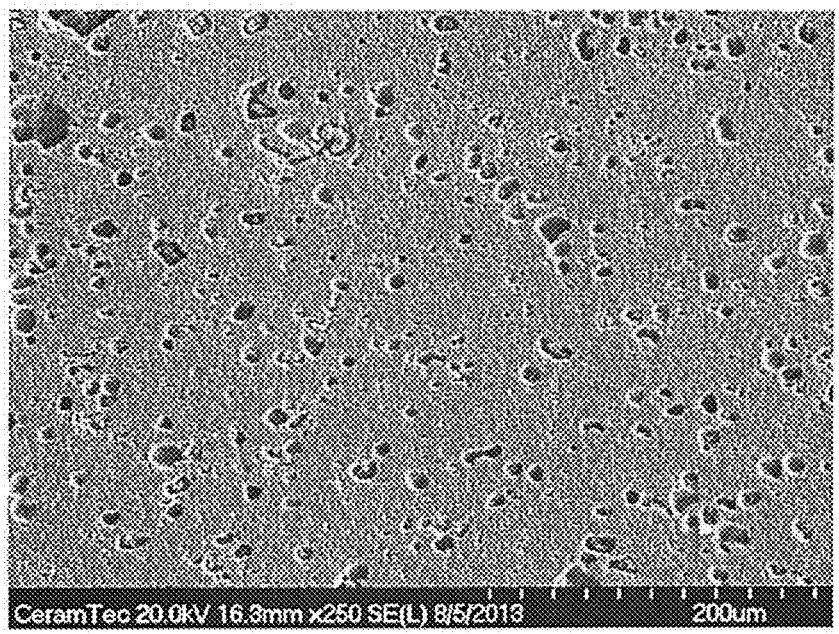
Figure 3B:
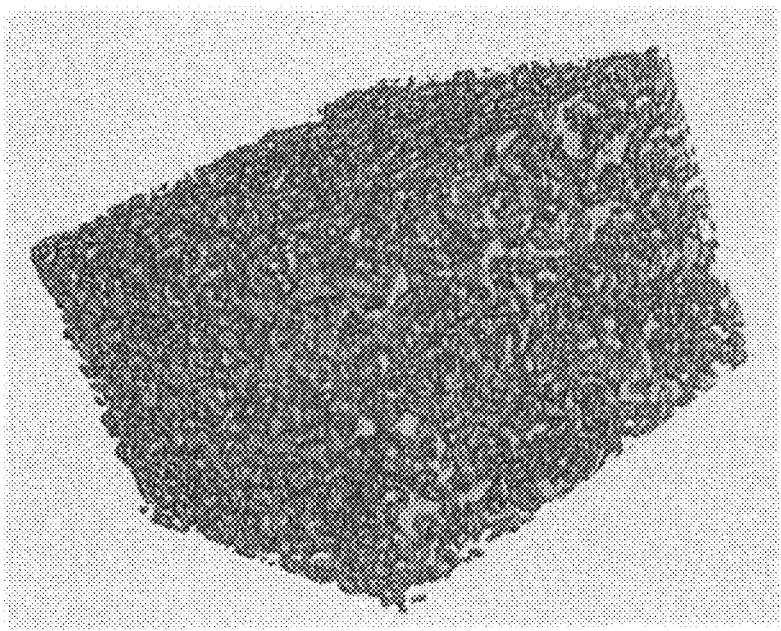

FIG. 3A shows a further embodiment of the porous filling material in a scanning electron micrograph of a ground section and the associated computer tomographic reconstruction of the pore network, see FIG. 3B. In contrast to the material shown in FIGS. 2A and 2B, a more fine-grained pore generator was used here for generating porosity, namely maize semolina with grain sizes between 5 and 50 µm. This porosity is also percolating, although the pore volume proportion is markedly lower at approx. 25 vol % compared to the example shown in FIG. 2. As a ceramic material, a ZTA ceramic was used.

Figure 4:
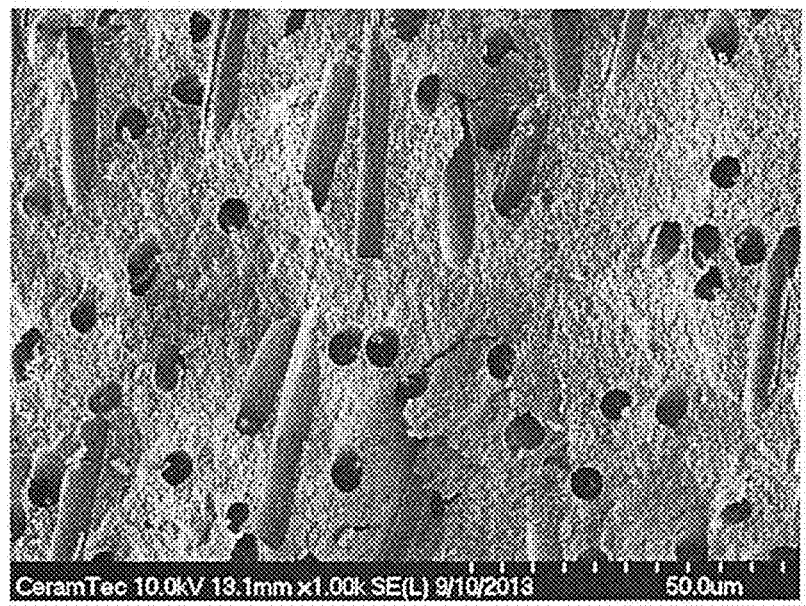

FIG. 4 shows a further embodiment of the porous filling from a Y-stabilised TZP ceramic. As a pore generator, carbon fibres with a diameter of 7 µm and a length of 150 µm were used.

The invention claimed is:

1. An implant, comprising a solid, load-bearing shell, a porous filling material having a porous network and directed pore channels, wherein the directed pore channels pass through the porous filling material, wherein the pore volume proportion of the shell is less than 3 vol % and wherein the pore volume of the porous filling material is from 15 to 50%.

2. The implant as claimed in claim 1, wherein the shell comprises a ceramic material.

3. The implant as claimed in claim 1, wherein the pore volume of the porous filling material is between 25 and 50 vol %.

4. The implant as claimed in claim 1, wherein the porosity of the filling material is percolating.

5. The implant as claimed in claim 1, wherein the porous filling material has pore sizes in the range of 2 to 400 µm.

6. The implant as claimed in claim 1, wherein the pore channels of the porous filling material have an average diameter of 0.1 to 2 mm.

7. The implant as claimed in claim 1, wherein walls of the pore channels have a surface roughness with an average roughness depth of Rz 10 to 250 µm.

8. The implant as claimed in claim 7, wherein the pore volume proportion of the shell is less than 2 vol %.

9. The implant as claimed in claim 7, wherein the pore volume proportion of the shell is less than 1 vol %.

10. The implant as claimed in claim 7, wherein the porous filling material has pore sizes in the range of 2 to 400 µm.

11. The implant as claimed in claim 1, wherein the pore channels are in hydraulic contact with the porosity of the filling material.

12. A method for producing a ceramic implant according to claim 1 comprising producing the ceramic implant via a ceramic two-component injection moulding method, wherein the ceramic implant comprises a solid, load-bearing shell and a porous filling material.

13. The method as claimed in claim 12, wherein a first and a second feedstock are formed from at least one mixture of ceramic powder and at least one wax-like polymer preparation, wherein the second feedstock additionally comprises combustible pore generators.

14. The method as claimed in claim 13, wherein the same mixture of ceramic powder or different mixes of ceramic powder are used for the first and the second feedstock.

15. The method as claimed in claim 12, wherein the pore generators are selected from the group consisting of maize semolina, melamine resin particles, polyamide particles, carbon particles, glassy carbon particles, carbon fibers, poppy seeds and cereal flour.

16. The method as claimed in claim 12, wherein an injection moulding tool having pin-like components is used, so that during injection moulding continuous pore channels are generated in the material of the second feedstock.

17. The method as claimed in claim 12, wherein by post-processing the green body or the finished sintered ceramic implant, continuous pore channels are generated in the material of the second feedstock.

18. The implant as claimed in claim 1, wherein the filling material comprises a ceramic.

19. The implant as claimed in claim 1, wherein the pore volume proportion of the shell is less than 2 vol %.

20. The implant as claimed in claim 1, wherein the pore volume proportion of the shell is less than 1 vol %.

* * * * *